(12) United States Patent
Riondel et al.

(10) Patent No.: US 9,776,946 B2
(45) Date of Patent: Oct. 3, 2017

(54) PROCESS FOR PRODUCING 2-PROPYLHEPTYL ACRYLATE BY TRANSESTERIFICATION

(71) Applicant: Arkema France, Colombes (FR)

(72) Inventors: Alain F. Riondel, Saint Pathus (FR); Coralie Graire, Grezieu-la-Varenne (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 14/771,820

(22) PCT Filed: Feb. 24, 2014

(86) PCT No.: PCT/FR2014/050367
§ 371 (c)(1),
(2) Date: Sep. 1, 2015

(87) PCT Pub. No.: WO2014/131970
PCT Pub. Date: Sep. 4, 2014

(65) Prior Publication Data
US 2016/0023985 A1 Jan. 28, 2016

(30) Foreign Application Priority Data

Mar. 1, 2013 (FR) ..................... 13 51838

(51) Int. Cl.
*C07C 67/03* (2006.01)
*C07C 67/54* (2006.01)

(52) U.S. Cl.
CPC .............. *C07C 67/03* (2013.01); *C07C 67/54* (2013.01)

(58) Field of Classification Search
None
See application file for complete search history.

(56) References Cited

U.S. PATENT DOCUMENTS 6,977,310 B2 12/2005 Ackermann et al.
7,268,251 B2 9/2007 Geisendoerfer et al.

FOREIGN PATENT DOCUMENTS

JP 5070403 A 3/1993

OTHER PUBLICATIONS

Machine translation for JP H05-070403 A Mar. 23, 1993.*
Propylheptanol-Technical data sheet, BASF, Feb. 2007.*

* cited by examiner

*Primary Examiner* — Sudhakar Katakam
*Assistant Examiner* — Ana Z Muresan
(74) *Attorney, Agent, or Firm* — Lynn B. Morreale

(57) ABSTRACT

The invention relates to the industrial production of highly pure 2-propylheptyl acrylate with a high yield according to a process by transesterification, preferably in semi-continuous mode. The process according to the invention uses ethyl titanate in solution in 2-propylheptanol or 2-propylheptyl titanate as transesterification catalyst, and implements a purification sequence comprising a single distillation column and a film evaporator.

10 Claims, 1 Drawing Sheet

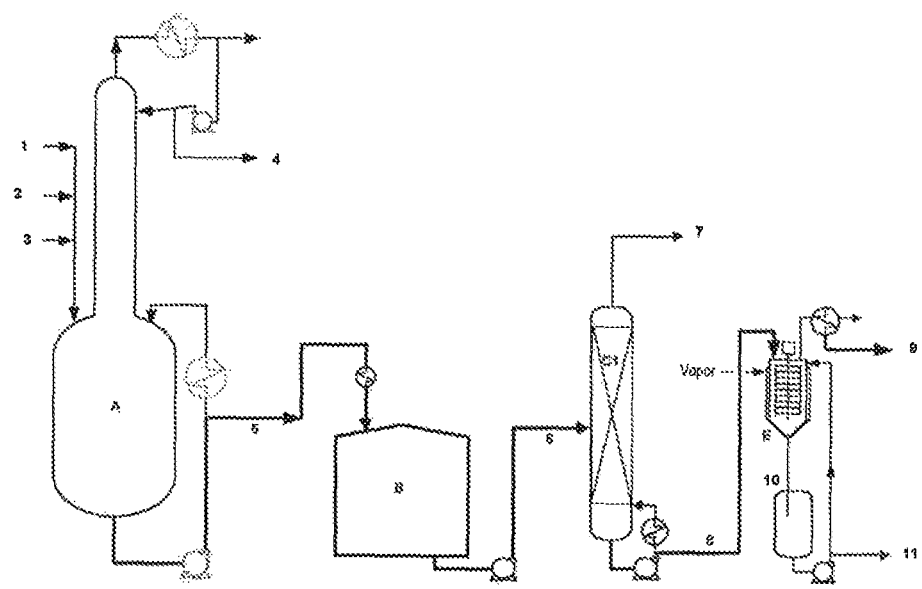

PROCESS FOR PRODUCING 2-PROPYLHEPTYL ACRYLATE BY TRANSESTERIFICATION

CROSS-REFERENCE TO RELATED APPLICATIONS

This application is a national stage application under 35 U.S.C. §371 of PCT/FR2014/050367, filed Feb. 24, 2014, which claims benefit to French patent application FR13.51838, filed Mar. 1, 2013.

FIELD OF THE INVENTION

The present invention relates to the production of 2-propylheptyl acrylate according to a semicontinuous transesterification process.

TECHNICAL BACKGROUND

It is known to produce acrylic esters by carrying out a transesterification reaction between a light alkyl acrylate (known as light acrylate) and a heavy alcohol.

This reaction is an equilibrated catalyzed reaction with generation of light alcohol, according to the formula (I):

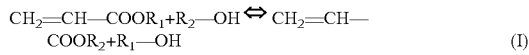

$$CH_2=CH-COOR_1+R_2-OH \Leftrightarrow CH_2=CH-COOR_2+R_1-OH \qquad (I)$$

It is necessary to remove the light alcohol produced during the reaction in order to shift the equilibrium in the direction of the production of the acrylic ester.

This reaction is generally accompanied by side reactions which produce impurities which it is necessary to remove for the purpose of obtaining the acrylic ester with a high purity which meets the technical requirements related to its final use as monomer for manufacturing polymers which can be used in numerous fields of application.

Furthermore, for obvious economical reasons, the products of economic value present in the crude reaction mixture, in particular the unreacted reactants and the catalyst, are as far as possible recycled in the process.

For these purposes, a separation/purification process comprising a combination of distillations, extractions and/or separations by settling is generally carried out, which process is simultaneously relatively complex to carry out, in particular as a result of the presence of azeotropic mixtures, and expensive energetically.

The applicant company has been concerned more particularly with the synthesis of 2-propylheptyl acrylate (alkyl acrylate with a branched $C_{10}$ chain) from a light acrylate and 2-propylheptanol (known as 2-PH), it being possible for this monomer to exhibit advantageous properties in the field of coating materials, paints, inks and adhesives.

According to the document JP05-070403, 2-propylheptyl acrylate can be obtained by direct esterification of acrylic acid or by transesterification of a light acrylate, such as methyl acrylate, with 2-propylheptanol in the presence of p-toluenesulfonic acid as catalyst and of a polymerization inhibitor, according to methods well known to a person skilled in the art. The methanol formed is continuously removed and the reaction is followed by a distillation under reduced pressure by way of purification of the reaction product obtained. The document JP05-070403 does not clearly mention the stages of purification to be carried out or the level of purity to be expected for the monomer for the purpose of the use thereof.

Various transesterification processes for producing $C_2$-$C_{12}$ alkyl acrylates have already been described in the prior art.

Mention may be made, for example, of the document U.S. Pat. No. 7,268,251, in which the reaction effluent stream from the transesterification is treated in the following way:

either most of the acrylic ester desired is first of all separated and is subsequently isolated from the catalyst used by distillation (separation of catalyst), or the catalyst used is first of all isolated by distillation (separation of catalyst) and subsequently most of the acrylic ester is separated, and subsequently the compounds having a lower boiling point than that of the desired acrylic ester are separated by distillation from the mixture obtained (separation of the low-boiling-point substances) and subsequently the acrylic ester is distilled (distillation in the pure state).

This process requires the use of at least four distillation or rectification columns, including an evaporator in order to separate the catalyst, generally a titanium alkoxide.

Even if the process described in the document U.S. Pat. No. 7,268,251 relates to the manufacture of alkyl acrylates by transesterification starting from an alkyl acrylate and from an alcohol exhibiting a chain length greater by at least one carbon with respect to the alkyl chain of the starting acrylate, this process is illustrated only with the manufacture of dimethylaminoethyl acrylate from dimethylaminoethanol and from methyl acrylate or ethyl acrylate in a cascade of two reactors.

It turns out that the process described in the document U.S. Pat. No. 7,268,251 is complicated to carry out on an industrial scale, as a result of the optimization of the operating conditions of the sequence of the four distillation/rectification components, in order to obtain a product of high purity and a satisfactory productivity.

The document U.S. Pat. No. 6,977,310 describes a process for the continuous manufacture of (meth)acrylic acid alkyl esters from methyl (meth)acrylate and a $C_2$-$C_{12}$ alcohol in the presence of a tetraalkyl titanate as transesterification catalyst. This process consists in subjecting the reaction mixture to a distillation under reduced pressure which separates the readily volatile compounds (unreacted reactants); then, the resulting fraction exiting at the column bottom, comprising the ester produced, the catalyst, the polymerization inhibitors and the high-boiling-point byproducts, is sent to a vacuum distillation stage. This vacuum distillation stage comprises in particular a film evaporator, combined with a distillation column, for complete removal of the high-boiling-point products in the ester produced. The ester produced is recovered at the top with a high purity.

According to this process, illustrated solely with the manufacture of butyl methacrylate or isobutyl methacrylate, the desired methacrylate occurs in the bottom stream from the first column for distillation under reduced pressure, before being separated from the catalyst and then purified.

The processes of the prior art using alkyl titanate, such as tetraethyl titanate, tetrabutyl titanate or tetra(2-ethylhexyl) titanate as transesterification catalyst, are not directly applicable to the manufacture of long-chain alkyl acrylate, for example 2-propylheptyl acrylate, by transesterification reaction of a light acrylate with 2-propylheptanol. This is because the transesterification of titanates, either with the light alcohol released during the reaction (methanol or ethanol) or with the starting 2-propylheptanol, brings about the appearance of impurities, such as butyl acrylate or 2-ethylhexyl acrylate, in the reaction mixture or in the light ester/light alcohol azeotropic mixture and complicates the purification of the 2-propylheptyl acrylate.

The applicant company has attempted to solve the various problems of the abovementioned processes, in particular those related to the use of 2-propylheptanol in the transesterification reaction catalyzed by an alkyl titanate, and has discovered a simplified manufacturing process for producing 2-propylheptyl acrylate of very high purity with a high yield, while including the recycling of the products of economic value, such as the unreacted reactants and the catalyst, thus exhibiting a productivity compatible with manufacture on an industrial scale.

The solution provided consists in using ethyl titanate in solution in 2-propylheptanol or 2-propylheptyl titanate as transesterification catalyst and in employing a purification line comprising only a single distillation column and a film evaporator.

Furthermore, the inventors have found that tin derivatives, in particular dibutyltin oxide, as transesterification catalysts also make it possible to overcome the disadvantages of the abovementioned processes and can be used to produce 2-propylheptyl acrylate in a transesterification process comprising a simplified purification line with just one distillation column and a film evaporator.

SUMMARY OF THE INVENTION

A subject matter of the present invention is a process for the production of 2-propylheptyl acrylate by a transesterification reaction between a light alkyl acrylate and 2-propylheptanol in the presence of an alkyl titanate as transesterification catalyst and of at least one polymerization inhibitor, the azeotropic mixture composed of light alkyl acrylate and light alcohol generated by the transesterification reaction being continuously withdrawn during the reaction and the reaction mixture being subjected to a purification treatment in order to obtain a 2-propylheptyl acrylate of high purity, which process is characterized in that:
- the catalyst is chosen from ethyl titanate in solution in 2-propylheptanol and 2-propylheptyl titanate;
- the crude reaction mixture comprising the desired 2-propylheptyl acrylate with, as light products, the unreacted light alkyl acrylate and traces of 2-propylheptanol and, as heavy products, the catalyst, the polymerization inhibitor(s) and also heavy reaction byproducts is sent to a distillation column (C1) under reduced pressure, and a distillation is carried out, in said column (C1), which makes it possible to obtain:
  - at the top, a stream essentially composed of unreacted light alkyl acrylate with traces of 2-propylheptanol, and
  - at the bottom, a stream essentially composed of desired 2-propylheptyl acrylate, with the catalyst, the polymerization inhibitor(s) and also heavy reaction byproducts, and traces of light compounds; then
- the bottom stream from the distillation column (C1) is sent to a film evaporator under reduced pressure, making it possible to separate:
  - at the top, the desired pure 2-propylheptyl acrylate; and
  - at the bottom, the catalyst, the polymerization inhibitor(s) and also the heavy reaction byproducts.

In the present invention, "light alkyl acrylate" or "light acrylate" have the same meaning and mean an acrylic ester comprising a short alkyl chain, that is to say comprising a linear $C_1$-$C_4$ alkyl chain, the light alkyl being derived from a linear $C_1$-$C_4$ alcohol.

The invention is now described in more detail and without implied limitation in the description which follows, with reference to the single appended FIGURE, which diagrammatically represents a plant which makes possible the implementation of the process according to the invention.

DETAILED DESCRIPTION

The process for the production of 2-propylheptyl acrylate according to the invention can be a batch process, a continuous process or a semicontinuous process, that is to say with the reaction part batchwise and the purification part continuous. Preferably, the process according to the invention is semicontinuous.

The alcohol, 2-propylheptanol, used in the process according to the invention can be represented in the form: $C_5H_{11}CH(C_3H_7)CH_2OH$, with it being possible for the $C_5H_{11}$ group to represent n-$C_5H_{11}$, $C_2H_5CH(CH_3)CH_2$ or $CH_3CH(CH_3)CH_2CH_2$.

The simplified name 2-PH in the continuation of the description is understood to mean 2-propylheptanol in the form of each of these isomers, alone or as a mixture. The 2-PH can additionally comprise a low content of other isomers, such as 2-isopropylheptanol, 2-isopropyl-4-methylhexanol, 2-isopropyl-5-methylhexanol or 2-propyl-4,4-dimethylpentanol.

The 2-PH can be produced in various ways, for example by aldolization of n-valeraldehyde produced by hydroformylation of butenes, dehydration of the alcohol obtained to give 2-propyl-2-heptanol, followed by hydrogenation.

The 2-PH can also be obtained by condensation of 1-pentanol (in the form of a mixture of methylbutanols) in the presence of KOH at a high temperature according to a Guerbet reaction.

According to the invention, the 2-PH predominantly comprises 2-propylheptanol. In general, the 2-PH is a mixture comprising:
- from 70 to 99%, preferably from 80 to 95%, of 2-propylheptanol n-$C_5H_{11}CH(C_3H_7)CH_2OH$ and
- from 1 to 30%, preferably from 5 to 20%, of a mixture of 4-methyl-2-propylhexanol $C_2H_5CH(CH_3)CH_2CH(C_3H_7)CH_2OH$ and 5-methyl-2-propylhexanol $CH_3CH(CH_3)CH_2CH_2CH(C_3H_7)CH_2OH$.

2-Propylheptanol is sold in particular by BASF.

Use is made, as light alkyl acrylate employed as starting material in the process according to the invention, of methyl acrylate, ethyl acrylate or butyl acrylate, preferably ethyl acrylate.

The light alky acrylate is obtained by direct esterification of acrylic acid, essentially produced industrially from propylene, with a light alcohol, general methanol, ethanol or butanol.

The invention applies to the use of a light alkyl acrylate derived from acrylic acid of renewable origin, which can in particular be obtained from glycerol according to a process comprising a first stage of dehydration of the glycerol to give acrolein, followed by a stage of gas-phase oxidation of the acrolein thus obtained, or obtained by dehydration of 2-hydroxypropionic acid (lactic acid) or 3-hydroxypropionic acid and their esters.

The invention also applies to the use of a light alkyl acrylate derived from a biosourced alcohol, such as bioethanol.

Generally, the transesterification reaction is carried out in a stirred reactor (A), heated by an external exchanger surmounted by a distillation column, in the presence of an excess of light alkyl acrylate, in particular with a light alkyl acrylate/2-PH molar ratio which can range from 1 to 3, preferably of between 1.3 and 1.8.

The transesterification catalyst is ethyl titanate in solution in 2-PH, for example a 90% solution of ethyl titanate in 2-PH, or 2-propylheptyl titanate, obtained beforehand by reaction at 100° C. of ethyl titanate with 2-PH; preferably, ethyl titanate in solution in 2-PH is used.

The invention applies to the use of tin derivatives as transesterification catalysts, such as dialkyltin oxides, the linear or branched alkyl chain having from 1 to 8 carbon atoms. Mention may be made, as examples, of dialkyltin oxides with a linear alkyl chain having from 1 to 4 carbon atoms, such as dimethyltin oxide, diethyltin oxide or more particularly di(n-butyl)tin oxide (DBTO).

The catalyst is used in a proportion of $5.10^{-4}$ to $5.10^{-2}$ mol per mole of 2-PH, preferably in a proportion of $10^{-3}$ to $10^{-2}$ mol per mole of 2-PH.

The transesterification reaction is generally carried out in the reactor (A) at a pressure of between 200 mmHg ($0.27 \times 10^5$ Pa) and atmospheric pressure and at a temperature ranging from 90° C. to 130° C., preferably from 95° C. to 110° C.

The reaction is carried out in the presence of one or more polymerization inhibitors which are introduced into the reactor in a proportion of 10 to 5000 ppm, with respect to the crude reaction mixture, and preferably of 200 to 1000 ppm.

Mention may be made, as polymerization inhibitors which can be used, for example, of phenothiazine, hydroquinone, hydroquinone monomethyl ether (HOME), di(tert-butyl)-para-cresol (BHT), TEMPO (2,2,6,6-tetramethyl-1-piperidinyloxy), di(tert-butyl)catechol or TEMPO derivatives, such as 4-hydroxy-TEMPO (4-OHTEMPO), alone or their mixtures in all proportions. Preferably, hydroquinone monomethyl ether (HOME) is used as polymerization inhibitor.

A supplementary addition of polymerization inhibitor is generally carried out in the distillation column surmounting the reactor and during the subsequent purification treatment, in particular in the distillation column (C1), and in the final product downstream of the top condenser of the film evaporator.

The light alcohol (generally methanol or ethanol) formed by the transesterification reaction is continuously entrained by distillation in the column surmounting the reactor in the form of an azeotropic mixture with the light alky acrylate. This mixture is advantageously recycled to the unit for the synthesis of the light acrylate. This synthesis unit proceeds according to direct esterification of acrylic acid with the light alcohol.

After reaction with a residence time in the reactor generally of between 3 and 6 hours, the crude reaction mixture 5 comprises the desired 2-propylheptyl acrylate with, as light products, the unreacted light alkyl acrylate and traces of 2-HP and, as heavy products, the catalyst, the polymerization inhibitor or inhibitors and also heavy reaction byproducts.

In the case where the process is carried out according to a semicontinuous mode, the reaction mixture is stored in a buffer tank (B) before being subjected to the purification treatment.

The purification treatment comprises a distillation column (C1), generally also denoted stripping column by a person skilled in the art, in which air is sent into the bottom, and a film evaporator, in order to obtain, in separate fractions, the pure 2-propylheptyl acrylate, the light alkyl acrylate present in excess in the reaction mixture, and the catalyst with the polymerization inhibitor(s) and the heavy reaction byproducts.

The distillation column (C1) generally operates under pressure ranging from 10 to 50 mmHg ($0.013 \times 10^5$ Pa to $0.067 \times 10^5$ Pa) at a bottom temperature ranging from 90° C. to 150° C.

The top stream 7 from the column (C1) is mainly composed of unreacted light alkyl acrylate with traces of 2-PH. This stream 7 is preferably condensed and recovered in order to be recycled to the transesterification reaction in the reactor (A). However, this stream, present in a low amount, can be simply discarded in aqueous effluent streams from the process via a column for washing the vents.

The bottom stream 8 from the column (C1) is mainly composed of desired 2-propylheptyl acrylate with the catalyst, the polymerization inhibitors and the heavy byproducts and can comprise residual traces of light compounds (unreacted reactants).

This stream 8 is sent to a film evaporator (E) in order to separate the catalyst from the finished product, the separation of the catalyst in the "stripped" mixture not requiring the use of a distillation column. The purified 2-propylheptyl acrylate 9 is separated at the top and a fraction 10 comprising the catalyst, the polymerization inhibitors and also the heavy reaction byproducts is separated at the bottom.

A part 11 of this stream 10 can optionally be recycled in the reaction in the reactor (A), the remainder being discarded and incinerated in order to prevent an excessively great accumulation of heavy byproducts in the reactor.

Use may in particular be made, as film evaporator, of a falling film evaporator or a wiped film evaporator. This type of evaporator gives the advantage of having a reduced residence time which limits the formation of additional heavy compounds downstream of the reaction section. This evaporator is essentially composed of a cylindrical part heated by a jacket, of an upper part used for the separation of the vapors and of a rotor rotating at high speed. The stream to be treated is spread over the entire heating surface in the form of a highly turbulent film. The vapors which are formed rise countercurrentwise toward the top of the device. The nonevaporated products, essentially the catalyst, the polymerization inhibitors and the heavy byproducts, reach the lower part of the evaporator and are discharged in the form of the stream 10. The gas stream 9, at the top of the evaporator, consists of the purified desired product.

The film evaporator operates under pressure conditions of the order of 10 mbar and at a temperate of the order of 160° C.

The process for the manufacture of 2-propylheptyl acrylate according to the invention exhibits a productivity compatible with manufacture on an industrial scale and results in a 2-propylheptyl acrylate with a purity of greater than 99.5% meeting the purity requirements related to its final use, in particular with regard to the possibility of using this monomer in the manufacture of latexes having a low content of volatile organic compounds in the fields, for example, of adhesives, coatings, paints or inks.

Experimental Part

In the examples, the percentages are shown by weight, unless otherwise indicated, and the following abbreviations have been used:

EA: ethyl acrylate
2-PH: 2-propylheptanol
2PHA: 2-propylheptyl acrylate
HQME: hydroquinone methyl ether Example 1 (According to the Invention)

387 g of 2-propylheptanol (2-PH, stream 1), 490 g of ethyl acrylate (EA, stream 2) and 1.31 g of ethyl titanate in solution in 2-PH (85% mixture in 2-PH) with 0.13 g of HQME (stream 3) are charged, under bubbling with air in order to stabilize the reaction medium, into a perfectly stirred 1 L reactor A heated by an external exchanger of thermosiphon type surmounted by a distillation column comprising a stacked packing of Multiknit type with 12 theoretical plates. Ami/tune comprising 500 ppm of HQME in EA is introduced at the top of the distillation column (not represented).

The oil bath is brought to a temperature of 125° C. and the EA/ethanol azeotrope (4) is distilled continuously.

The pressure at the column top is regulated in order for the temperature in the reactor not to exceed 95° C.

During this stage, the pressure varies between 631 and 324 mbars and 166 g of EA/ethanol azeotrope comprising 69% by weight of ethanol are collected. The duration of the reaction is 3 hours.

The crude reaction product 5 (weight 652 g) has the following composition by weight:
  EA: 20.5%
  2-PH (sum of the isomers): 0.27%
  2PHA (sum of the isomers): 78.47%
  Catalyst+stabilizer+impurities: 0.76%

The crude reaction product is stored in a buffer tank B which continuously feeds a distillation column (C1) in the top part via a stream 6.

The column C1 is a column comprising a stacked packing of Multiknit type with seven theoretical plates operating under reduced pressure and heated by an external exchanger of thermosiphon type. A mixture comprising 500 ppm of HQME in EA is introduced at the top of column C1 (not represented).

The column C1 operates under vacuum (20-30 mbars, 100° C. max) and separates:
  at the top, a stream 7 comprising 99.5% of EA (138 g/h); and
  at the bottom, a stream 8 of crude 2PHA (514 g/h) with the composition by weight:
    EA: 0.1%
    2-PH (sum of the isomers): 0.25%
    2PHA (sum of the isomers): 98.69%
    Catalyst+stabilizer+impurities: 0.96%

The stream 7 of EA is sent to an intermediate tank (not represented in the diagram) in order to be recycled to the reaction.

The stream 8 of crude 2PHA is sent continuously to a film evaporator E which operates under reduced pressure (10 mbars, 160° C.).

The film evaporator separates:
  at the top, a stream 9 of purified 2PHA (463 g/h) with the composition by weight:
    2PHA (sum of the isomers): 99.57%
    EA: 0.15%
    2-PH (sum of the isomers): 0.27%
    HQME stabilizer: 250 ppm
  at the bottom, a stream 10 comprising a mixture of heavy byproducts and the catalyst (52 g/h), which is optionally recycled in part 11 to the reaction, the remainder being discarded.

Example 2 (Comparative)

The same synthesis as that described in example 1 is carried out using butyl titanate as catalyst.

In this case, the top stream 7 of EA resulting from the column C1 comprises 10% of butyl acrylate (BuA), which renders it unsuitable for recycling in this state in the reaction stage, and requires an additional distillation column in order to separate the EA from the butyl acrylate.

Example 3 (Comparative)

The same synthesis as that described in example 1 is carried out using 2-ethylhexyl titanate as catalyst.

In this case, the purity of the 2PHA in the stream 9 at the top of the film evaporator is only 97.5% due to the presence of 2% of 2-ethylhexyl acrylate. This grade of 2PHA does not offer the same performance in pressure-sensitive adhesives as a 2PHA with a purity of 99.5%.

The invention claimed is:

1. A process for the production of 2-propylheptyl acrylate by a transesterification reaction between light alkyl acrylate and 2-propylheptanol in the presence of catalyst selected from the group consisting of ethyl titanate in solution in 2-propylheptanol and 2-propylheptyl titanate and at least one polymerization inhibitor, an azeotropic mixture comprising light alkyl acrylate and light alcohol generated by the transesterification reaction being continuously withdrawn during the reaction and the reaction mixture being subjected to a purification to obtain a 2-propylheptyl acrylate of high purity, the process comprising the following steps:
   selecting the catalyst from the group consisting of ethyl titanate in solution in 2-propylheptanol and 2-propylheptyl titanate;
   purifying a crude reaction mixture by sending said crude reaction mixture to a purification line comprising a single distillation column (C1) under reduced pressure and a single film evaporator, said purification line having no other distillation column or film evaporator, said crude reaction mixture comprising 2-propylheptyl acrylate, light products comprising unreacted light alkyl acrylate and traces of 2-propylheptanol and heavy products comprising catalyst, polymerization inhibitor(s) and heavy-reaction-byproducts, and
   distilling said crude reaction mixture in said single distillation column (C1), to obtain:
     at top, a stream comprising unreacted light alkyl acrylate with traces of 2-propylheptanol, and
     at bottom, a stream comprising 2-propylheptyl acrylate, with catalyst, polymerization inhibitor(s) and heavy reaction byproducts, and traces of light compounds; then
   sending the bottom stream from the distillation column (C1) to a film evaporator (E) under reduced pressure, to separate:
     at top, purified 2-propylheptyl acrylate having a purity greater than 99.5%; and
     at bottom, catalyst, polymerization inhibitor(s) and heavy reaction byproducts.

2. The process of claim 1, wherein the catalyst is ethyl titanate in solution in 2-propylheptanol.

3. The process of claim 1 carried out in batch, continuous or semicontinuous mode.

4. The process of claim 1 wherein the 2-propylheptanol is a mixture comprising:
- from 70 to 99% of 2-propylheptanol n-$C_5H_{11}CH(C_3H_7)$ $CH_2OH$ and
- from 1 to 30% of a mixture of 4-methyl-2-propyl-hexanol $C_2H_5CH(CH_3)CH_2CH(C_3H_7)CH_2OH$ and 5-methyl-2-propylhexanol $CH_3CH(CH_3)CH_2CH_2CH(C_3H_7)CH_2OH$.

5. The process of claim 1 wherein the light alkyl acrylate is ethyl acrylate.

6. The process of claim 1 wherein the film evaporator is a falling film evaporator or a wiped film evaporator.

7. The process of claim 1 wherein the top stream of the column C1 is recycled to the reaction.

8. The process of claim 1 wherein the stream separated at the bottom of the film evaporator is recycled at least in part to the reaction.

9. The process of claim 1 wherein the azeotropic mixture comprising light alkyl acrylate and light alcohol generated by the transesterification reaction is recycled to the unit for the synthesis of the light alkyl acrylate.

10. The process of claim 1 wherein the polymerization inhibitor is hydroquinone monomethyl ether (HQME).

* * * * *